(12) United States Patent
Mücke et al.

(10) Patent No.: US 7,101,697 B2
(45) Date of Patent: Sep. 5, 2006

(54) RESTRICTION ENDONUCLEASES, METHOD OF SYNTHESIS AND USE THEREOF

(75) Inventors: Merlind Mücke, Berlin (DE); Monika Reuter, Berlin (DE); Detlev Krüger, Stahnsdorf (DE)

(73) Assignee: Charité—Universitätsmedizin Berlin, Berlin (DE)

( * ) Notice: Subject to any disclaimer, the term of this patent is extended or adjusted under 35 U.S.C. 154(b) by 371 days.

(21) Appl. No.: 10/425,031

(22) Filed: Apr. 29, 2003

(65) Prior Publication Data

US 2004/0091892 A1   May 13, 2004

(30) Foreign Application Priority Data

Apr. 30, 2002  (DE) ............................... 102 20 953
Jul. 19, 2002   (DE) ............................... 102 33 958

(51) Int. Cl.
  *C12N 9/22*   (2006.01)
  *C12P 19/34*  (2006.01)

(52) U.S. Cl. ..................................... 435/199; 435/91.1

(58) Field of Classification Search ................ 435/199, 435/91.1
See application file for complete search history.

(56) References Cited

U.S. PATENT DOCUMENTS 5,292,651 A * 3/1994 Guthrie et al. .............. 435/199
5,356,802 A * 10/1994 Chandrasegaran .......... 435/199
5,436,150 A * 7/1995 Chandrasegaran .......... 435/199

OTHER PUBLICATIONS

M. Mücke, et al. EcoRII: a restriction enzyme evolving recombination functions?, The EMBO Journal, vol. 21, No. 19, pp. 5262-5268 (2002).

M. L. Embleton et al., DNA cleavage reactions by type II restriction enzymes that require two copies of their recognition sites, J. Mol. Biol., vol. 311, No. 3, pp. 503-514 (2001).

E. A. Karpova et al., A Model of EcoRII restriction endonuclease action: The active complex is most likely formed by one protein subunit and one DNA recognition site, IUBMB Life, vol. 48, pp. 91-98 (1999).

M. Reuter, et al., Regions of endonuclease EcoRII involved in DNA target recognition identified by membrane-bound peptide repertoires, J. Biol. Chem., vol. 274, No. 8, pp. 5213-5221 (1999).

O.V. Petrauskene, et al., EcoRII endonuclease has two identical DNA-binding sites and cleaves one of two coordinated recognition sites in one catalytic event, FEBS Lett., vol. 425, No. 1, pp. 29-34 (1998).

M. Reuter, et al., Cooperative Binding Properties of Restriction Endonuclease EcoRII with DNA Recognition Sites, The Journal of Biological Chemistry, vol. 273, No. 14, pp. 8294-8300 (1998).

S. Gabbara and A.S. Bhagwat, Interaction of EcoRII Endonuclease with DNA Substrates Containing Single Recognition Sites, The Journal of Biological Chemistry, vol. 267, No. 26, pp. 18623-18630 (1992).

O.V. Petrauskene, et al., Mechanism of the Interaction of EcoRII restriction endonuclease with two recognition sites, Eur. J. Biochem., vol. 208, pp. 617-622 (1992).

J.D. Colandene, The domain organization of NaeI endonuclease: separation of binding and catalysis, PNAS vol. 95, pp. 3531-3536 (1998).

Q. Huai, et al., Crystal structure of NaeI—an evolutionary bridge between DNA endonuclease and topoisomerase, The EMBO Journal vol. 19, pp. 3110-3118 (2000).

Reuter, et al. Regions of endonuclease EcoRII involved in DNA target recognition identified by membrane-bound peptide repertoires, J. Biol. Chem. vol. 274 (8), 5213-5221, Database Genebank, registry No. AJ224995 of Oct. 8, 1999.

A.S. Bhagwat, et al., Primary sequence of the EcoRII endonuclease and properties of its fusions with beta-galactosidase, J. Biol. Chem., vol. 265(2), pp. 767-773, (1990), Database PRF, registry No. prf_1603301A.

Database SWISS-PROT. registry No. spT2E2_ECOLI of Oct. 16, 2001 and multiple comparison of sequences between SEQ ID No. 1 and sequence form (3) and (5).

Database SWISS-PROT. registry No. spT2N1_NOCAE from Oct. 16, 2001.

* cited by examiner

*Primary Examiner*—Charles L. Patterson, Jr.
(74) *Attorney, Agent, or Firm*—Rothwell, Figg, Ernst & Manbeck

(57) ABSTRACT

A restriction endonuclease having one DNA binding site is proposed, synthesized from a restriction endonuclease that has one C-terminal domain and one N-terminal domain and two DNA binding sites, by proteolytic cleavage into the two domains or by cloning the gene segment that codes for the domains and expression of the domains and selection of the endonucleolytic domains having one DNA binding site. In addition, a method of synthesis of the restriction endonuclease and its use are claimed.

13 Claims, 3 Drawing Sheets

RESTRICTION ENDONUCLEASES, METHOD OF SYNTHESIS AND USE THEREOF

Figure 1:
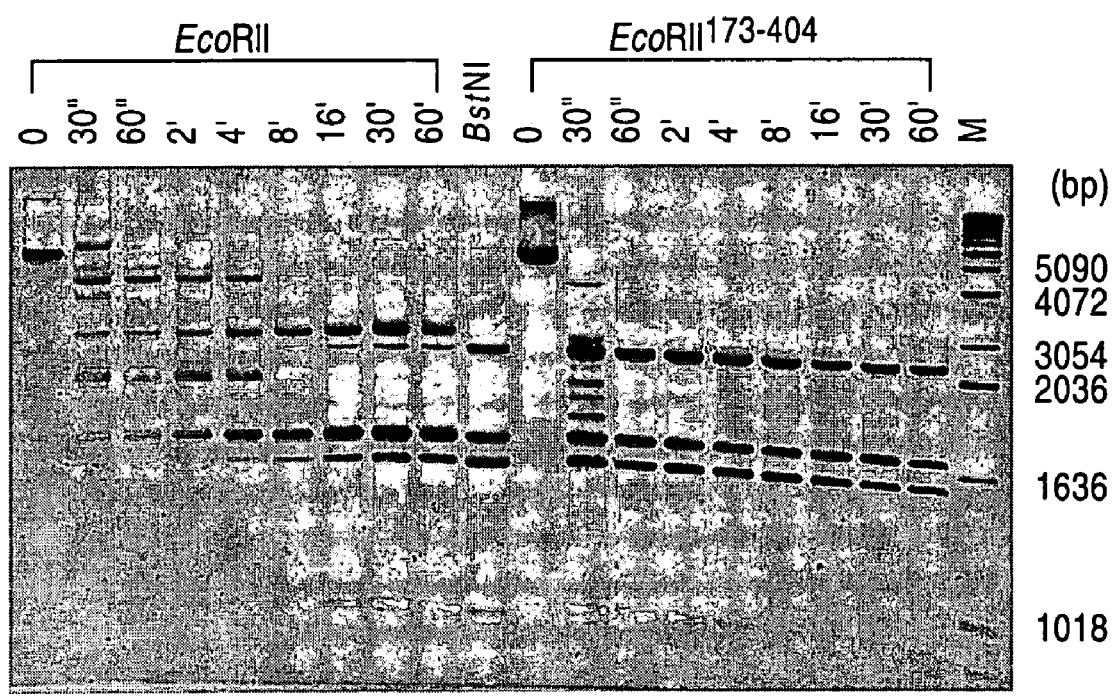

This invention relates to novel active restriction endonucleases, methods of synthesis of and use thereof. The areas of application of this invention are in genetic engineering and functional genome analysis.

Restriction endonucleases are used for specific cleavage of DNA molecules to analyze the DNA, to recombine the resulting DNA cleavage products in a controlled manner, to detect specific methylation of individual nucleotides and to study protein-protein and protein-ligand interactions.

Restriction endonucleases, i.e., restriction enzymes, are usually proteins of a bacterial origin which cleave the phosphodiester bonds in the area of defined base sequences in both strands of a DNA molecule. Such restrictions result in DNA cleavage products known as DNA restriction fragments. Only through the availability of restriction endonucleases has it become possible to break down DNA into defined fragments or components in vitro and thus make it accessible for further techniques of genetic engineering, such as gene mapping or cloning. Restriction endonucleases are therefore some of the most important enzymes for genetic experiments and biotechnology methods.

Restriction endonucleases are divided into three classes, namely type I, type II and type III. Type I restriction nucleases consist of three subunits and recognize a specific DNA sequence, but then they cut the DNA at a random position. Type III restriction endonucleases consist of two subunits, recognize specific DNA sequences and cleave the DNA at a location 20 to 25 nucleotides away from that. Type II restriction nucleases are the only ones which cleave DNA at precisely defined locations, the cleavage site usually being within the recognition sequence. Most of the type II restriction endonucleases used in the laboratory today recognize a sequence consisting of 4, 6 or 8 bases. Restriction enzymes which recognize a sequence of five bases are used somewhat less commonly in laboratories.

The known orthodox type II restriction endonucleases recognize specifically short palindromic DNA sequences and cleave the DNA endonucleolytically and specifically within or near this DNA sequence. The restriction endonucleases are thus able to cleave DNA molecules, so that blunt ends or 5'- or 3'-overhanging ends, so-called cohesive ends, are formed. For example, the restriction endonuclease EcoRII creates cleavage products or DNA fragments with 5'-cohesive ends from *Escherichia coli* (therefore Eco, the gene coded by the resistance plasmid R), and in contrast with other known type II restriction endonucleases, it requires simultaneous interaction with two copies of their DNA recognition sequence ("site"). The DNA recognition sequence of EcoRII consists of the 5'-CCWGG nucleotide sequence. EcoRII is the prototype of an entire group of type II restriction endonucleases requiring an interaction with two copies of their recognition sequence or two sites for their endonucleolytic activity. Due to the essential interaction with two sites, cleavage of DNA by EcoRII proceeds more slowly in comparison with so-called orthodox restriction endonucleases, and/or no cleavage takes place at all in the case of a low occurrence of recognition sequences in a DNA substrate.

Restriction endonucleases can be used not only for cutting DNA molecules but also for DNA methylation studies. The protection against penetrating foreign DNA which is provided for bacteria by restriction endonucleases is based on differentiation of the DNA endogenous to the bacteria from foreign DNA based on the specific methylation pattern. Therefore, specifically methylated DNA recognition sequences cannot be recognized by many restriction endonucleases and consequently cannot be digested or cleaved. However, there are endorestriction nucleases [sic; restriction endonucleases] which have a different methylation sensitivity, i.e., certain restriction enzymes also recognize and cleave methylated DNA strands. Restriction endonucleases which recognize the same sequence and cleave it in different ways are known as isoschizomers; for example, BstNI is a restriction endonuclease which is isoschizomeric to EcoRII. By comparing the DNA fragments generated by the isoschizomers, it is possible to determine the methylation of the original DNA on the basis of the different methylation sensitivity with the same recognition sequence.

Although restriction digestion of DNA with restriction endonucleases is one of the most common experiments used today in the field of basic research or clinical research, there are many disadvantages to working with these enzymes. Many restriction endonucleases will not cleave DNA completely, in particular those which must interact with multiple recognition sequences to cleave DNA endonucleolytically. Although almost all the starting material—the DNA—is cleaved at least once after a certain period of time, the number of completely digested DNA fragments (in the sense of all sites being cleaved) is too low. However, even such incomplete fragmentation requires up to one or two hours. Previous attempts to optimize the incomplete cleavage in a shorter period of time have included increasing the salt concentration of the buffer, lowering the pH, preventing the use of organic solvents or a low glycerol concentration. However, these modifications of the experimental setup first result in relaxation of the specificity of the restriction endonucleases and, secondly, the amount of completely cleaved fragments is not increased. In addition, it is possible to increase endonucleolytic cleavage by adding specific oligonucleotides. However, adding such oligonucleotides is a disadvantage for other process steps.

Therefore, the object of this invention is to make available restriction endonucleases which will cleave DNA more efficiently and in particular completely, whose specificity will be unchanged and which will have a greater activity in comparison with known restriction endonucleases, and these novel restriction endonucleases should be simple and inexpensive to produce.

This technical problem is solved by the invention by providing restriction endonucleases having one DNA binding site produced from a restriction endonuclease which has a C-terminal domain and an N-terminal domain and two DNA binding sites by proteolytic cleavage into the two domains or by determining the crystal structure of the domains and selecting and cloning the gene segment which codes for the domains and expressing the domains and then selecting the nucleolytic domains that have a DNA binding site.

Restriction endonucleases comprising two domains, a C-terminal domain and an N-terminal domain, and therefore having two DNA binding pockets or DNA binding sites can be separated into their domains. For example, treating the restriction endonucleases with proteases results in an original restriction endonuclease, in particular a type II restriction endonuclease, being cleaved proteolytically into its two domains, thus yielding the N- and C-terminal domains separately from one another. By methods with which those skilled in the art are familiar, it is then possible to select the endonucleolytic domains, i.e., the domains capable of cleaving DNA endonucleolytically, i.e., enzymatically. In contrast with the restriction endonucleases used originally, these endonucleolytic domains no longer have two DNA binding pockets, but instead they have only one DNA binding pocket or DNA binding sequence. For example, it is possible to cleave the EcoRII restriction endonuclease by a protease such as trypsin to yield the N- and C-terminal domains, and then to select the endonucleolytic domain, namely the C-terminal domain in the present case. Because this endonucleolytic C-terminal domain has only one DNA binding pocket or DNA binding site, in contrast with the complete enzyme EcoRII, which can cleave DNA only by interaction with two recognition sites on the DNA, it needs only one recognition site to cleave DNA. Thus, the restriction endonuclease according to this invention more rapidly and more efficiently binds and cuts the DNA to be fragmented.

Structural models, in particular crystal structures, are known for some restriction endonucleases. For example, there are several structural models of the restriction endonuclease NaeI. On the basis of these models, those skilled in the art are able to determine the size of individual domains. In the case of NaeI, for example, it is possible to ascertain on the basis of the known crystal structures, which amino acid sequences form the N-terminal domain and the C-terminal domain. According to methods with which those skilled in the art are familiar, it is then possible to select the gene segments which code for the corresponding domains, then clone them, express them and subsequently select the nucleolytic domain having one DNA binding site. The term "expression" as used here is understood to describe the transcription and/or coding of the sequence of a domain. In expression, first a DNA chain which codes the sequence of a domain is transcribed into a complementary RNA, which is frequently an mRNA. Then the mRNA thus transcribed is translated to the domain mentioned above. Expression also includes transcription of a DNA which has been inserted in anti-sense direction with respect to its regulation elements. Expression that is constitutive and might be further enhanced by an externally controlled promoter fragment also includes the formation of multiple RNA copies and production of large amounts of the selected domains, i.e., it also includes overproduction of domains.

Those skilled in the art will be aware here of the fact that the domains may be linked together by a hinge-loop region. This region is partially responsible for the spatial arrangement of the domains. It is not critical in which area of the hinge-loop those skilled in the art would cleave the domains. It is important that a complete domain must be obtained, but the extent to which a shorter or longer area of the hinge-loop region is present on this complete domain is less important. Thus, the domains are produced in particular by determining the crystal structure, selecting a gene segment that codes for a domain, cloning, and expressing the domains. The domains thus obtained are then purified by known methods of protein chemistry, e.g., by chromatography.

For example, it is possible for the two domains to be obtained by column chromatography, e.g., by gel filtration by preparative gel electrophoresis or by ammonium sulfate precipitation, ion exchangers, isoelectric focusing, chromatofocusing, by separation with the help of hydroxylapatite, by lectin chromatography, ligand chromatography or other methods with which those skilled in the art are familiar. The separated domains can be fractionated and/or aliquoted, for example, during this isolation and recovery. By testing individual fractions or aliquots for their endonucleolytic or nucleolytic activity, it is possible to select the fraction containing the nucleolytic domain in a targeted manner. This invention describes for the first time how a novel, effectively cleaving restriction endonuclease is generated by fragmenting or truncating a restriction endonuclease with two binding sequences. The novel restriction endonuclease is advantageously capable of generating cohesive ends in particular, which are advantageous for ligation or binding of specific sequences.

In a preferred embodiment, these restriction endonucleases are type II restriction endonucleases. In an especially preferred embodiment of this invention, the restriction endonucleases according to this invention are produced from EcoRII, NaeI, Alw26I, BbvI, BsrI, EarI, NarI, BspMI, HpaII, SacII, Eco57I, AtuBI, Cfr9I, SauBMKI, Ksp632I, HphI, MboII, SfaNI or Tth111I, and most especially preferably from EcoRII. These restriction endonucleases advantageously cleave the sequence which they also recognize, i.e., the fragmentation, cutting or cleaving of the DNA does not take place outside of the sequence recognized by the restriction endonuclease.

In another preferred embodiment of this invention, the restriction endonuclease having one binding site includes the amino acid sequence SLQQAPVNHKYILPEDWHLRF-PSGSEIIQYAASHYVKNSLDPDEQLLDRRRVEY DIFLLVEELHVLDIIRKGFGSVDEFI-ALANSVSNRRKSRAGKSLELHLEHLFIEHGLRHFAT QAITEGNKKPDFLFPSAGAYHDTEF-PVENLRMLAVKTTCKDRWRQILNEADKIHQVHLF TLQEGVSLAQYREMRESGVRLVVPSSLH-KKYPEAVRAELMTLGAFIAELTGLYADIP (SEQ ID NO: 1) or an amino acid sequence that is at least 80% homologous with it, preferably at least 90%. The term "amino acid sequence" refers to the part of the amino acid sequence that is coded by a gene segment, not including the regulation sequences that control the initiation or termination of transcription. The amino acid sequence and/or the amino acid sequence that is at least 80% homologous with it, preferably at least 90%, refers to the naturally occurring amino acid sequence as well as any desired modifications, mutants or derivatives of any of the fragments of these amino acids. The amino acid modifications may include, for example, inversions, deletions, insertions, substitutions, additions, denaturing or oxidation. This homology may be determined, e.g., by the Smith-Waterman homology search algorithm, e.g., with the MPSRCH program (Oxford Molecular), using an affinity gap search with the following parameters: gap open penalty 12, gap extension penalty 1.

From the structural analysis, e.g., the x-ray crystal structural analysis, those skilled in the art will be aware that the domains in restriction endonucleases are joined by bonding sequences of different lengths—the hinge-loop region—which essentially fulfills the function of determining a certain spatial arrangement of the domains relative to one another. Those skilled in the art can select the amino acid sequence or the gene segment coding for the N- or C-terminal domain, so that only the domain having components of the hinge-loop region of different lengths is obtained. The domain in the sense of this invention may therefore be the actual domain, i.e., the domain with a portion of the hinge-loop and/or the entire hinge-loop region. Therefore, those skilled in the art will be aware of the fact that the amino acid sequence of the restriction endonuclease may comprise approximately ±6 additional amino acids. It is of course also possible for His$_6$-tag sequences or the like which are used for protein purification to be attached to the amino acid sequence. In another preferred embodiment of this invention, the restriction endonuclease includes the amino acid sequence MTELPLQFAEPDDDLERVRATLYSLDP-DGDRTAGVLRDTLDQLYDGQRTGRWNFDQLH KTEKTHMGTLVEINLHREFQFGDGFET-
DYEIAGVQVDCKFSMSQGAWMLPPESIGHICL
VIWASDQQCAWTAGLVKVIPQFLGTAN-
RDLKRRLTPEGRAQVVKLW (SEQ ID NO: 2) or an amino acid sequence which is at least 80% homologous with this, preferably at least 90%.

This amino acid sequence may also include other amino acids of the hinge-loop region, as explained above.

This invention also relates to a method of producing restriction endonucleases having one DNA binding site, whereby the N- and C-terminal domains are separated proteolytically from a restriction endonuclease having two DNA binding sites and two domains, the endonucleolytic domains are isolated and the novel active restriction endonuclease is obtained. This method of preparing the novel active restriction endonucleases thus consists of proteolytic separation of a restriction endonuclease, preferably type II, particularly preferably type IIc and/or type IIs having two DNA binding pockets or DNA binding sites and two domains, to yield the N- and C-terminal domains. This proteolytic separation may be accomplished by proteases, for example. Those skilled in the art are aware of various suitable proteases. Proteases in the sense of this invention include all enzymes capable of catalyzing proteolytic cleavage of the protein bond in restriction endonucleases having two binding sites. These proteases may be, e.g., acidic, neutral or alkaline proteases. Endopeptidases in particular may be used for cleavage of the two domains. In particular, serine endopeptidases, cysteine endopeptidases, aspartic acid endopeptidases and/or metalloendopeptidases may be used. It is of course also possible to use proteases having a previously unknown catalytic mechanism; these include, for example, enzymes previously classified in enzyme group EC 3.4.99. After separating the two domains, the endonucleolytic domains are obtained and thus the novel restriction endonuclease is obtained. Those skilled in the art will be aware of various possibilities for obtaining the nucleolytic domain, e.g., isolation by column chromatography.

In another advantageous embodiment of this invention, restriction endonucleases having two binding sites and two domains are cleaved with a protease, preferably trypsin or chymotrypsin. The proteases may be selected advantageously by those skilled in the art such that they are capable of cleaving restriction endonucleases into functional domains, so that C- or N-terminal endonucleolytic domains having one binding site are obtained. For example, trypsin cleaves preferentially at arginine and lysine. Chymotrypsin is a protease which cleaves preferentially on the carboxy side of aromatic amino acids such as tyrosine, tryptophan and phenylalanine as well as methionine. In addition to the preferred proteases, chymotrypsin and trypsin, in particular the proteases V8, elastase, thermitase, papain, pepsin, mycolysin and others may also be used.

In another preferred embodiment of this invention, restriction endonucleases having two DNA binding sites or DNA binding pockets that are used include EcoRII, NaeI, Alw26I, BbvI, BsrI, EarI, NarI, BspMI, HpaII, SacII, Eco57I, AtuBI, Cfr9I, SauBMKI, Ksp632I, HphI, MboII, SfaNI or Tth111I. These restriction endonucleases are preferably type II, in particular type IIe and type IIs restriction endonucleases.

This invention also relates to a method of producing a restriction endonuclease having one DNA binding site or DNA binding pocket by the methods of genetic engineering, whereby a gene segment which codes for the nucleolytic C- or N-terminal domain is cloned and expressed, the gene product thus obtained is purified, and thus the restriction endonuclease having one DNA binding site is obtained. In the method of producing restriction endonucleases by genetic engineering, the gene segment that codes for the endonucleolytic C- or N-terminal domain is cloned by methods with which those skilled in the art are familiar. For example, it is possible for those skilled in the art to first perform a proteolytic cleavage of the restriction endonuclease and thus isolate the nucleolytic domain as described above. However, they could also sequence the nucleolytic domain after proteolytic cleavage and, on the basis of this information, select the proper coding gene segment for further synthesis of the nucleolytic domain by genetic engineering. However, it is also possible for those skilled in the art to select the nucleolytic C- or N-terminal domain on the basis of structural analyses and thus select the gene segment that codes for the nucleolytic domain for synthesis by genetic engineering. The gene segment can be selected here to include all or part or none of a part of the hinge-loop region. After those skilled in the art have selected the gene segment that codes for the nucleolytic C- or N-terminal domain, it is cloned. After isolation and replication of the specific DNA gene segment, the nucleolytic domain is obtained by polymerase chain reaction or by known methods in which the DNA gene segment is linked to a vector and replicated in a host organism or a cell.

In another special embodiment, the gene segment that codes for the following amino acid sequence is used:
SLQQAPVNHKYILPEDWHLRFPSGSEI-
IQYAASHYVKNSLDPDEQLLDRRRVEY DIFLLVEEL-
HVLDIIRKGFGSVDEFIALANSVSNRRK-
SRAGKSLELHLEHLFIEHGLRHFATQ
AITEGNKKPDFLFPSAGAYHDTEFPVEN-
LRMLAVKTTCKDRWRQILNEADKIHQVHLFTL
QEGVSLAQYREMRESGVRLVVPSSLH-
KKYPEAVRAELMTLGAFIAELTGLYADIP (SEQ ID NO: 1)

or MTELPLQFAEPDDDLERVRATLYSLDP-
DGDRTAGVLRDTLDQLYDGQRTGRWNFDQLH
KTEKTHMGTLVEINLHREFQFGDGFET-
DYEIAGVQVDCKFSMSQGAWMLPPESIGHICLV
IWASDQQCAWTAGLVKVIPQFLGTAN-
RDLKRRLTPEGRAQVVKLW (SEQ ID NO: 2).

The term "gene segment" as used here denotes in this connection a DNA sequence that codes for the N- and/or C-terminal domain and regulation elements that control expression of this DNA sequence. The term "coding sequence" here refers to that portion of the gene which codes for a C- and/or N-terminal domain and/or the N-terminal domain and a portion of the hinge-loop region, not including the regulation sequences, which control the initiation or termination of transcription. The coding sequence or regulation element may be one normally present in the cell, the so-called autologous elements, or it may be one not normally located in the cell, i.e., heterologous elements. After the selected gene segments that code for the nucleolytic domain have been cloned, they may be expressed either in liposomes without cells or in a suitable host cell. Expressing here means that the sequence of the gene product is transcribed and/or coded, i.e., in expression, first a DNA chain that codes for the sequence of the nucleolytic domain is transcribed to a complementary RNA, and then the mRNA thus transcribed is translated into the above-mentioned gene product, the nucleolytic domain. The nucleolytic domain obtained in this way can be isolated and purified by known methods.

This invention also relates to the use of the proteins or domains synthesized by the method according to this invention as restriction endonucleases. The domains, protein fragments or peptides thus obtained can be used to advantage as enzymes for cleavage of DNA. With the help of the proteins thus obtained, it is possible to cleave DNA without the known disadvantages because the proteins do not require the essential interaction with two recognition sequences. The proteins themselves have only one DNA binding site or binding pocket, so that the interaction with one recognition sequence is advantageously sufficient. For the endonucleolytic effect of the proteins thus obtained, it is adequate if the one binding sequence interacts with the substrate, i.e., with the DNA, so therefore the protein thus obtained cleaves DNA more rapidly and more completely than do the known enzymes. In a preferred embodiment, the amino acid sequences ID No. 1 or ID No. 2 or amino acid sequences that are at least 80% homologous with these sequences, preferably at least 90% homologous, are used as the restriction endonuclease.

In a particularly preferred embodiment, the restriction endonucleases according to this invention or the aforementioned domains are used for cleavage of DNA molecules or oligonucleotide duplexes, for detection of DNA methylation, for genome analysis and for synthesis of base pair overhangs and for recombination of DNA molecules. DNA molecules or oligonucleotide duplexes can advantageously be cleaved rapidly and effectively with the restriction endonucleases according to this invention. The use of the novel restriction endonucleases thus involves cleavage of DNA molecules and oligonucleotide duplexes with a greater efficiency than was possible with the known restriction endonucleases, and in particular the problem of the dependence of the cleavage of the DNA on the presence of two recognition sequences, i.e., recognition sites, is eliminated. Another use is for effective determination of DNA methylation by comparative digestion with isoschizomeric restriction endonucleases. The original methylation-sensitive restriction endonuclease having two binding sites is optimized in its effect by using the nucleolytic, domains. For example, the natural DNA methylation 5-methylcytosine in the second position of the 5'-CCWGG sequence is detected by comparative cleavage with EcoRII and the isoschizomeric BstNI (from *Bacillus stearothermophilus* N) which is not sensitive to this methylation. EcoRII is prevented from cleaving the DNA here due to the above-mentioned methylation, but BstNI does cut the DNA after the second position—regardless of the presence of 5-methylcytosine. In the past, this determination of methylation has been compromised by the limited activity of EcoRII, because in the case of resistance of the corresponding DNA, it has not been possible to state with absolute certainty whether the lack of cleavage was due to the methylation or due to the rare presence of the recognition sequence in the DNA or the restricted activity of EcoRII. These sources of error can be ruled out by using the restriction endonucleases according to this invention, thus permitting more reliable detection of methylation by using the nucleolytic domain. Like the methylation determination, genome analysis is also improved by the restriction endonucleases according to this invention, e.g., typing of the hepatitis C virus genome is performed by investigating the restriction fragment length polymorphism (RFLP) with various restriction endonucleases. By using the restriction endonuclease according to this invention, this typing method is improved because the error source resulting from the restricted activity of the restriction endonuclease having two DNA binding pockets, e.g., in the case of EcoRII, is eliminated. In addition, the restriction endonucleases according to this invention, which are obtained from EcoRII, for example, are so far the only active restriction endonucleases that efficiently cleave the 5'-CCWGG DNA sequence having a 5-bp 5'-overhang at 37° C. and accept individual sites for endonucleolytic DNA cleavage. The high CG content of the cohesively cleaved ends is advantageous for ligation in particular because the specific sequence leads to so-called sticky ends. The restriction endonucleases according to this invention can also be used in cleavage of DNA molecules and for analysis of DNA and for recombining (cloning) them, and in particular for effective recombination of DNA molecules by producing especially cohesive ends. The restriction endonucleases according to this invention are also used for identification and characterization of DNA molecules or DNA genomes via defined restriction cleavage patterns. Such restriction cleavage patterns are understood to include a precisely defined number of DNA fragments of a defined size, which are formed by treating a certain DNA with a restriction endonuclease. These restriction cleavage patterns are visualized by gel electrophoresis.

The restriction endonucleases according to this invention have several advantages. In contrast to the restriction endonucleases from which they are obtained, they do not have two DNA binding sequences, sites or pockets, but instead they have only one, which interacts with the DNA, so the restriction endonucleases according to this invention cleave DNA very effectively and completely within an extremely short period of time, but there is no change in the specificity of the restriction endonucleases according to this invention in comparison with the restriction endonuclease having two binding sequences. These novel restriction endonucleases are derived from wild-type restriction endonucleases, for example, and in particular they constitute the shortened, truncated form thereof. Due to the fact that these novel restriction endonucleases have only one C- and/or N-terminal domain comprising a DNA binding sequence, they can be synthesized easily and inexpensively. It is therefore readily possible by using the known methods and processes to obtain the restriction endonucleases according to this invention by proteolysis and/or by genetic engineering methods. The genetic engineering methods may be of such a type that either cell-free systems such as PCR or systems that include cells, such as the transfection of mammalian or insect cells, for example, may be used. The restriction endonucleases according to this invention may be used to advantage in a wide variety of areas of fundamental research and clinical research. Since effect of the restriction endonucleases according to this invention is no longer compromised by the fact that they must interact with two recognition sequences to cleave DNA, they therefore cleave more effectively because an interaction with a single recognition sequence on the DNA molecule is sufficient. Therefore, the restriction endonuclease according to this invention can be used for numerous experiments, e.g., for detection of methylation and for studying protein-protein interactions and protein-ligand interactions.

With the help of the products according to this invention, it is possible to overcome the known disadvantages—delayed cleavage of DNA or none at all due to the essential interaction with two sites. Truncated EcoRII protein, for example, surprisingly cleaves DNA substrates independently of the occurrence of the sites in the DNA substrate, and does so with an activity that is far superior to that of the original complete EcoRII and corresponds to the activity of orthodox restriction endonucleases. The finding that truncation of a restriction endonuclease generates a novel, more active restriction endonuclease is essential to this invention and is described here for the first time.

This invention also consists of a combination of known elements—restriction endonucleases, detection of natural DNA methylation—and novel elements—truncated restriction endonucleases having a greater activity, more reliable detection of methylation, e.g., through the use of the truncated form of EcoRII. This results in DNA substrates being cleaved efficiently, regardless of the incidence of the sites in the DNA substrate.

The novel truncated restriction endonucleases according to this invention are used to advantage in genetic engineering, in genome analysis (including the characterization of genes by restriction fragment length polymorphism RFLP) and/or analysis of DNA according to molecular biology (including characterization of DNA molecules by restriction mapping), in particular when restriction endonucleases that do not depend on interaction with two DNA sites and thus also cleave individual sites effectively and specifically are needed.

Truncated restriction endonucleases may also be used for detection of sequences that include the corresponding DNA binding sites or cleavage sites for the restriction endonucleases. Selected genomes of disease pathogens may have such DNA binding sites and/or cleavage sites. For example, certain types or subtypes of a hepatitis C virus may include the CCWGG sequence, where W may denote A or T. With the help of the restriction endonucleases according to this invention, these virus types may be differentiated from types that do not have this sequence. By detecting sequences or cleavage fragments of the viral genome after treatment with the restriction endonuclease, which may be derived from EcoRII, for example, it is possible to ascertain by means of electrophoresis whether or not cleavage has taken place, thus providing information about the presence of the aforementioned sequence and therefore certain types or subtypes of the virus, i.e., pathogen.

This invention will now be described in greater detail on the basis of exemplary embodiments, although it is not restricted to these examples.

EXEMPLARY EMBODIMENTS

Synthesis/Production of Truncated Forms of Restriction Endonucleases

Truncated restriction endonucleases according to this invention are produced, e.g., by amplifying the particular gene segments of a wild-type restriction endonuclease by PCR (polymerase chain reaction), then cloning them in an expression vector, transforming them to a suitable cell and purifying the particular expressed truncated proteins of the restriction endonuclease. As an alternative, the wild-type protein may be shortened appropriately by proteolysis and purified.

The restriction endonuclease EcoRII, which codes for amino acids 173–404, is cloned in the pQE-30 vector (plasmid DNA, QIA express vector 30 which codes for N-terminal $His_6$-tag, among other things—6×histidine amino acid residue; reference: Qiagen, Heidelberg, Germany, Product Guide 2001, pp. 56–59, www.qiagen.com). Then *Escherichia coli* cells are transformed with this DNA construct. The expressed protein EcoRII-trunc or EcoRII-C is purified and characterized biochemically.

The methods according to this invention for obtaining truncated restriction endonucleases consist of cloning and expressing the shortened gene of the restriction endonuclease EcoRII, namely amino acids 173–404 of EcoRII, and purifying the gene product EcoRII-trunc, or proteolytically fragmenting the natural restriction endonuclease EcoRII by means of chymotrypsin in a controlled process and purifying the fragment consisting of amino acids 173–404 of EcoRII, namely EcoRII-trunc.

The truncated derivatives of type II restriction endonucleases according to this invention are thus shortened segments (fragments) of the restriction endonucleases, e.g., the truncated EcoRII protein (EcoRII-trunc) shortened by the portion of the natural EcoRII polypeptide chain formed by cleavage of a portion of the protein. In detail:

EXAMPLE 1

Cloning and Expression of Shortened Genes of Corresponding Restriction Endonucleases The segment of the gene of the restriction endonuclease EcoRII which codes for amino acids 173–404 was amplified by PCR. The PCR template was plasmid pQE-RII obtained from the pQE-30 expression vector (from Qiagen, Product Guide 2001, PP. 56–59, www.qiagen.com) (Reuter et al. (1998), *J. Biol. Chem.* 273, 8294–8300). PCR was performed with vent polymerase (New England Biolabs, www.neb.com) in the presence of 10% glycerol. The PCR primers 5'-CGCGGATCCT CTCTACAGCA AGCGC-CAGTA AATCATAAA (SEQ ID NO: 3) and 5'-GTAC-CTATGG AATATCTGCG TAAAGCCCTG (SEQ ID NO: 4) T were used for the protein EcoRII-trunc which was shortened at the N-terminus. The pQE-30 vector was cleaved with the restriction endonucleases SmaI and BamHI in succession and was dephosphorylated by alkaline phosphatase (Roche). The 703-bp-long PCR product was also cleaved with BamHI, phosphorylated with T4 polynucleotide kinase (New England Biolabs) and ATP and ligated with the help of T4 DNA ligase (New England Biolabs) into the previously opened pQE-30 vector. The resulting recombinant plasmid was tested by sequencing with the Thermosequenase Cycle Sequencing Kit (Amersham Biosciences) and then transformed in calcium dichloride-competent *Escherichia coli* JM109 (pDK1r$^-$m$^+$) cells. The amino acid positions are based on the EcoRII sequence AJ224995 which begins with Met$^3$ of EcoRII. The pQE-30 vector also codes for the N-terminal His6 tail of both mutants (amino acid sequence: MRGSHHHHHHGS, SEQ ID NO: 5). The EcoRII-trunc protein expressed with N-terminal $His_6$-tag was purified by affinity chromatography on a Ni-NTA column (Ni-NTA, nickel nitrilotriacetic acid from Qiagen, www.qiagen.com) (Reuter et al., *J. Biol. Chem.* (1998), 273, 8294–8300). Then the protein was purified by ion exchange chromatography on a heparin-agarose column (HiTrap heparin affinity columns from Amersham Biosciences, buffer A: 20 mM $K_2HPO_4$, pH 7.6; 2 mM ethylenediamine tetraacetic acid (EDTA); buffer B: 20 mM $K_2HPO_4/KH_2PO_4$, pH 7.6; 2 mM EDTA, 1M NaCl; linear gradient 0 to 100% buffer B in buffer A in 10 column volumes). EcoRII-trunc was stored in 50% glycerol; 200 mM NaCl; 20 mM Tris-HCl; pH 7.6; 1 mM EDTA; 1 mM β-mercaptoethanol at −20° C.

EXAMPLE 2

Limited Proteolysis of Natural Restriction Endonuclease Proteins

Proteolytic degradation of 400 µg EcoRII (4.3 nmol dimer) by chymotrypsin was performed at a mass ratio $m_{EcoRII}/m_{chymotrypsin}$ of 80/1 in 10 mM Tris-HCl, pH 8.5, in a reaction volume of 200 µL at 25° C. After four hours, the proteolysis reaction was stopped by adding PMSF protease inhibitor. After limited proteolysis, the truncated protein (EcoRII-trunc) was purified by anion exchange chromatography on a heparin-agarose column (HiTrap heparin affinity columns, Amersham Bioscience, determinations performed as in Example 1). The protein was stored as described in Example 1.

FIGURES

FIG. 1 shows that EcoRII-trunc cleaves nonmethylated DNA of pBR322 plasmid at a much higher rate and with a much greater efficiency than does natural EcoRII. The cleavage pattern shows that all 5'-CCWGC sites in the DNA molecule are cleaved by EcoRII-trunc in a sequence-specific manner. The cleavage pattern corresponds to that of the control generated by restriction endonuclease BstNI.

Figure 2:
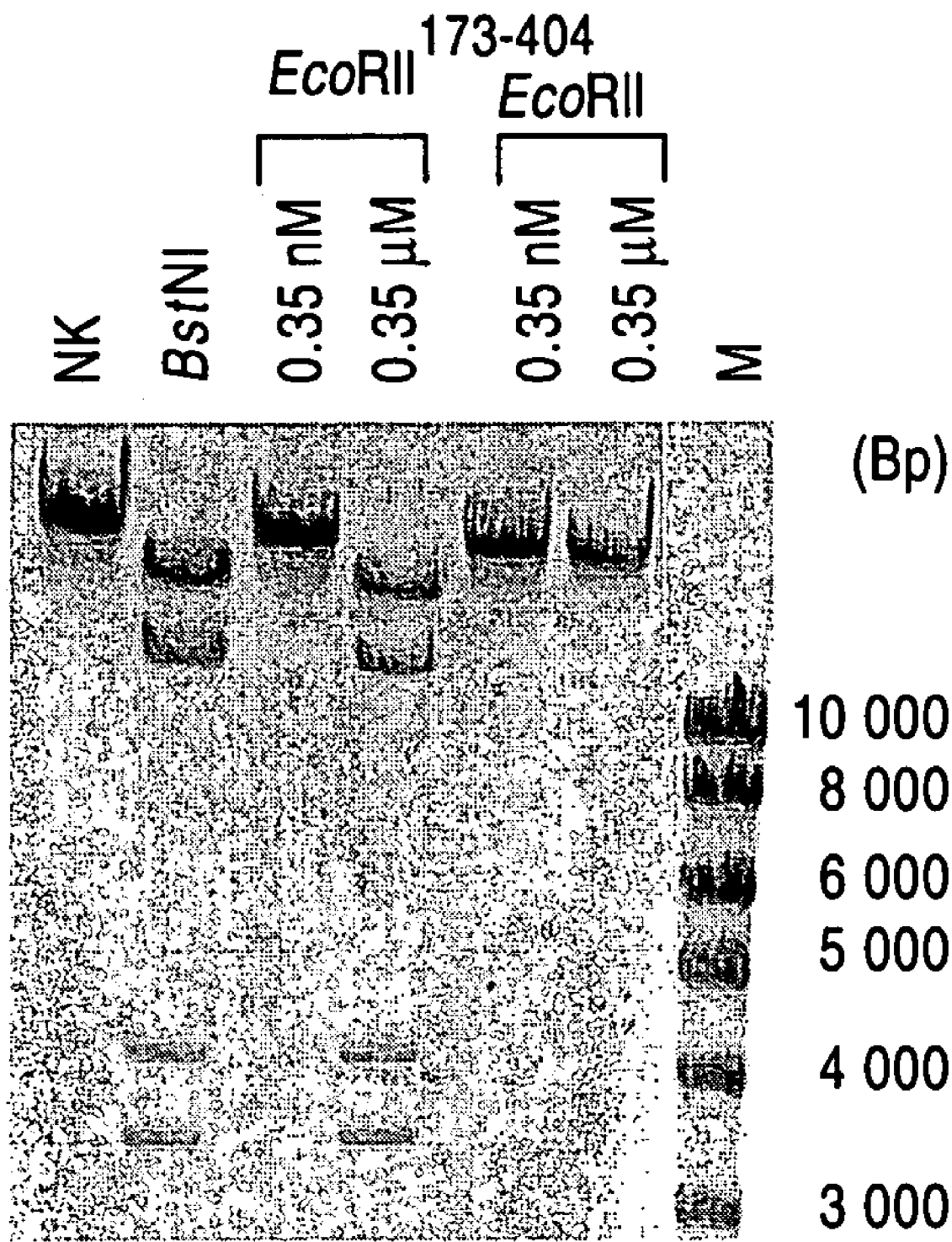

FIG. 2 shows clearly that the genomic DNA of bacteriophage T3, which cannot be cleaved by wild-type EcoRII because of the lower incidence of EcoRII sites, is specifically fragmented by EcoRII-trunc.

Figure 3:
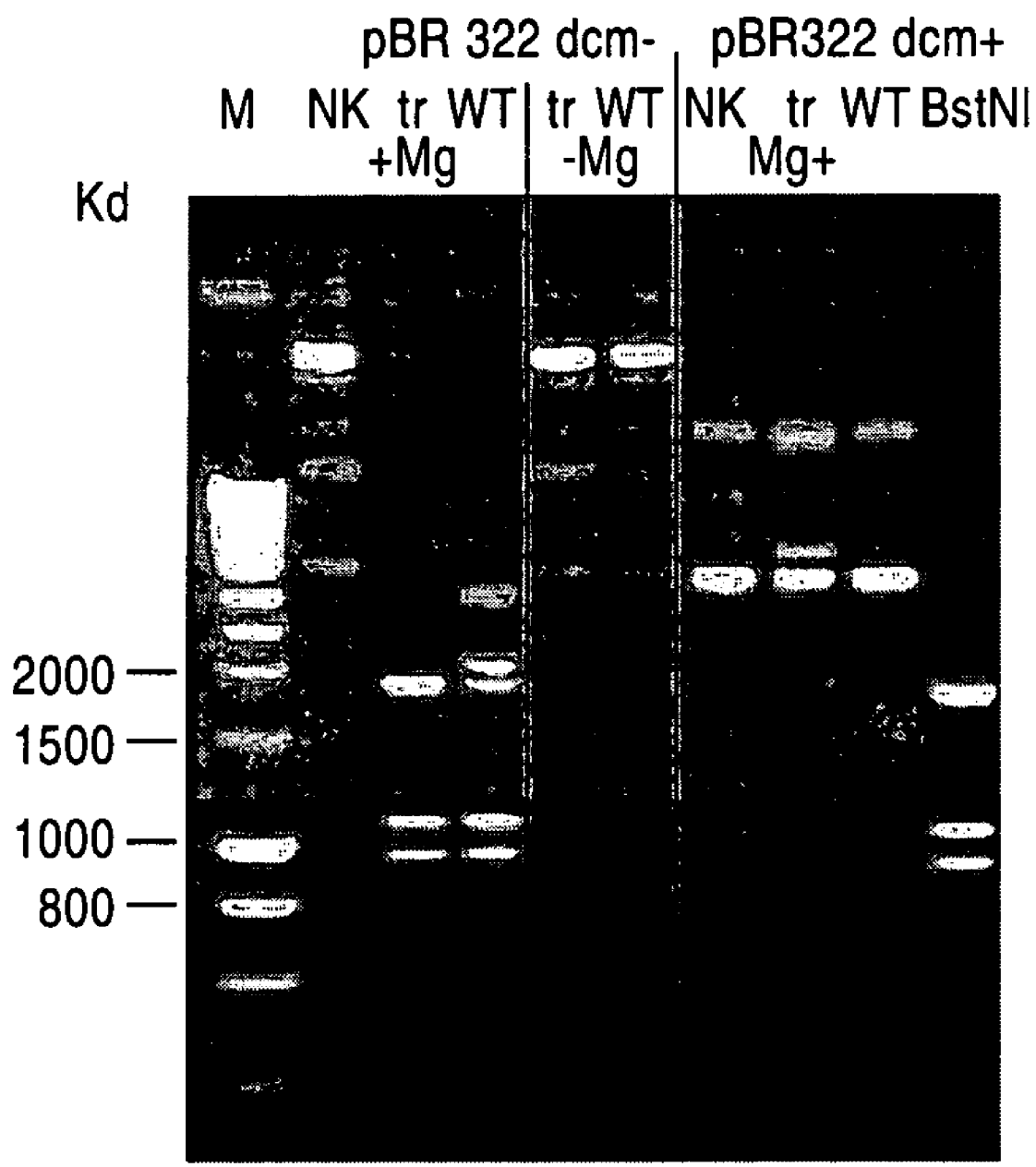

Finally, FIG. 3 proves that EcoRII-trunc is hindered in DNA cleavage by methylation of the second cytosine in the recognition sequence (site) just like the wild-type EcoRII. In contrast with unmethylated DNA (pBR322 dcm$^-$), EcoRII-specific methylated DNA (pBR322 dcm$^+$) is not cleaved by both enzymes. In addition, it is also demonstrated again that the DNA sequence specificity of EcoRII-trunc and wild-type EcoRII is identical, and that the activity of the two enzymes depends on the presence of Mg$^{2+}$ ions.

LEGENDS TO THE FIGURES

FIG. 1:
Kinetics of endonucleolytic hydrolysis of linearized nonmethylated DNA of the pBR322 plasmid (dcm$^-$) by wild-type EcoRII and EcoRII-trunc (here: EcoRII$^{173\text{-}404}$). This shows the electrophoretic separation of DNA molecules and fragments. At the top of the figure: reaction times; BstNI: positive control for the cleavage pattern due to cleavage with the isoschizomeric restriction endonuclease BstNI; M: molecular weight marker.

FIG. 2:
Cleavage of the DNA of bacteriophage T3 with EcoRII-trunc (here: EcoRII$^{173\text{-}404}$) and wild-type EcoRII. Top: quantities of enzymes used; left trace: T3 DNA without restriction endonuclease; BstNI: positive control of the cleavage pattern; right trace: molecular weight marker.

FIG. 3:
Comparison of sequence-specific recognition of the methylated recognition sequence by cleavage of methylated pBR322 DNA by EcoRII-trunc and wild-type EcoRII. From the left: M, molecular weight marker: negative control (NC), pBR322 dcm$^-$, and then succession, pBR322 dcm$^-$ DNA cleaved with: EcoRII-trunc and Mg$^{2+}$; wild-type EcoRII and Mg$^{2+}$; EcoRII-trunc without Mg$^{2+}$; wild-type EcoRII without Mg$^{2+}$; NK, pBR322 dcm$^+$ DNA (negative control); pBR322 dcm$^+$ DNA incubated with Mg$^{2+}$ and EcoRII-trunc and/or wild-type EcoRII; BstNI; cleavage with the isoschizomeric restriction endonuclease BstNI (positive control).

The invention claimed is:

1. A first restriction endonuclease having one DNA binding site, wherein said first restriction endonuclease is produced from a second restriction endonuclease, said second restriction endonuclease having a C-terminal domain, an N-terminal domain, and two DNA binding sites, wherein said first restriction endonuclease is produced by:
   i) proteolytically cleaving the C-terminal and N-terminal domains of the second restriction endonuclease and isolating a resulting nucleolytic domain having one DNA binding site; or
   ii) cloning a gene segment which codes for the domains of the second restriction endonuclease, expressing the domains, and isolating a resulting nucleolytic domain having one DNA binding site;
   and wherein the second restriction endonuclease is EcoRII.

2. The first restriction endonuclease of claim 1, wherein said first restriction endonuclease comprises SEQ ID NO: 1 or an amino acid sequence that is at least 95% homologous with SEQ ID NO: 1.

3. A method of cleaving a DNA comprising cleaving the DNA with an enzyme, wherein the enzyme comprises the first restriction endonuclease of claim 1.

4. The method of claim 3, wherein the first restriction endonuclease comprises SEQ ID NO: 1 or an amino acid sequence that is at least 95% homologous with SEQ ID NO: 1.

5. The method of claim 3, wherein the DNA comprises a DNA molecule or oligonucleotide duplexes.

6. The method of claim 3, wherein the DNA is cleaved for the detection of DNA methylation.

7. The method of claim 3, wherein the DNA is cleaved for genome analysis.

8. The method of claim 3, wherein the DNA is cleaved for synthesis of base pair overhangs and for recombination of DNA molecules.

9. A method of producing a restriction endonuclease having one DNA binding site, comprising:
   i) providing a second restriction endonuclease having a C-terminal domain, an N-terminal domain, and two DNA binding sites, wherein said second restriction endonuclease is EcoRII;
   ii) proteolytically cleaving the C-terminal and N-terminal domains of the second restriction endonuclease; and
   iii) isolating a resulting nucleolytic domain having one DNA binding site, thereby producing a restriction endonuclease having one DNA binding site.

10. The method of claim 9, characterized in that proteolytic cleavage is performed with a protease.

11. The method of claim 9, characterized in that proteolytic cleavage is performed with trypsin or chymotrypsin.

12. A method of producing a restriction endonuclease having one DNA binding site, comprising:
   i) providing a second restriction endonuclease having a C-terminal domain, an N-terminal domain, and two DNA binding sites, wherein said second restriction endonuclease is EcoRII;
   ii) cloning a gene segment which codes for the domains of the second restriction endonuclease and expressing the domains; and
   iii) isolating a resulting nucleolytic domain having one DNA binding site, thereby producing a restriction endonuclease having one DNA binding site.

13. The method of claim 12, characterized in that the gene segment is a gene segment that codes for SEQ ID NO: 1.

* * * * *

SEQUENCE LISTING

```
<160> NUMBER OF SEQ ID NOS: 5

<210> SEQ ID NO 1
<211> LENGTH: 232
<212> TYPE: PRT
<213> ORGANISM: Escherichia Coli

<400> SEQUENCE: 1

Ser Leu Gln Gln Ala Pro Val Asn His Lys Tyr Ile Leu Pro Glu Asp
1               5                   10                  15

Trp His Leu Arg Phe Pro Ser Gly Ser Glu Ile Ile Gln Tyr Ala Ala
            20                  25                  30

Ser His Tyr Val Lys Asn Ser Leu Asp Pro Asp Glu Gln Leu Leu Asp
        35                  40                  45

Arg Arg Arg Val Glu Tyr Asp Ile Phe Leu Leu Val Glu Glu Leu His
    50                  55                  60

Val Leu Asp Ile Ile Arg Lys Gly Phe Gly Ser Val Asp Glu Phe Ile
65                  70                  75                  80

Ala Leu Ala Asn Ser Val Ser Asn Arg Arg Lys Ser Arg Ala Gly Lys
                85                  90                  95

Ser Leu Glu Leu His Leu Glu His Leu Phe Ile Glu His Gly Leu Arg
            100                 105                 110

His Phe Ala Thr Gln Ala Ile Thr Glu Gly Asn Lys Lys Pro Asp Phe
        115                 120                 125

Leu Phe Pro Ser Ala Gly Ala Tyr His Asp Thr Glu Phe Pro Val Glu
    130                 135                 140
```

```
Asn Leu Arg Met Leu Ala Val Lys Thr Thr Cys Lys Asp Arg Trp Arg
145                 150                 155                 160

Gln Ile Leu Asn Glu Ala Asp Lys Ile His Gln Val His Leu Phe Thr
            165                 170                 175

Leu Gln Glu Gly Val Ser Leu Ala Gln Tyr Arg Glu Met Arg Glu Ser
            180                 185                 190

Gly Val Arg Leu Val Pro Ser Ser Leu His Lys Lys Tyr Pro Glu
        195                 200                 205

Ala Val Arg Ala Glu Leu Met Thr Leu Gly Ala Phe Ile Ala Glu Leu
        210                 215                 220

Thr Gly Leu Tyr Ala Asp Ile Pro
225                 230

<210> SEQ ID NO 2
<211> LENGTH: 163
<212> TYPE: PRT
<213> ORGANISM: Nocardia aerocolonigenes

<400> SEQUENCE: 2

Met Thr Glu Leu Pro Leu Gln Phe Ala Glu Pro Asp Asp Leu Glu
1               5                   10                  15

Arg Val Arg Ala Thr Leu Tyr Ser Leu Asp Pro Asp Gly Asp Arg Thr
            20                  25                  30

Ala Gly Val Leu Arg Asp Thr Leu Asp Gln Leu Tyr Asp Gly Gln Arg
        35                  40                  45

Thr Gly Arg Trp Asn Phe Asp Gln Leu His Lys Thr Glu Lys Thr His
    50                  55                  60

Met Gly Thr Leu Val Glu Ile Asn Leu His Arg Glu Phe Gln Phe Gly
65                  70                  75                  80

Asp Gly Phe Glu Thr Asp Tyr Glu Ile Ala Gly Val Gln Val Asp Cys
                85                  90                  95

Lys Phe Ser Met Ser Gln Gly Ala Trp Met Leu Pro Pro Glu Ser Ile
            100                 105                 110

Gly His Ile Cys Leu Val Ile Trp Ala Ser Asp Gln Gln Cys Ala Trp
        115                 120                 125

Thr Ala Gly Leu Val Lys Val Ile Pro Gln Phe Leu Gly Thr Ala Asn
    130                 135                 140

Arg Asp Leu Lys Arg Arg Leu Thr Pro Glu Gly Arg Ala Gln Val Val
145                 150                 155                 160

Lys Leu Trp

<210> SEQ ID NO 3
<211> LENGTH: 39
<212> TYPE: DNA
<213> ORGANISM: artificial sequence
<220> FEATURE:
<223> OTHER INFORMATION: oligo

<400> SEQUENCE: 3
cgcggatcct ctctacagca agcgccagta aatcataaa                          39

<210> SEQ ID NO 4
<211> LENGTH: 20
<212> TYPE: DNA
<213> ORGANISM: artificial sequence
<220> FEATURE:
<223> OTHER INFORMATION: oligo
```

```
-continued

<400> SEQUENCE: 4
gtacctatgg aatatctgcg                                                    20

<210> SEQ ID NO 5
<211> LENGTH: 12
<212> TYPE: PRT
<213> ORGANISM: pQE-30

<400> SEQUENCE: 5

Met Arg Gly Ser Gly Gly Gly Gly Gly Gly Gly Ser
1               5                   10
```